(12) United States Patent
Ichikawa (10) Patent No.: US 7,331,670 B2
(45) Date of Patent: Feb. 19, 2008

(54) FUNDUS CAMERA

(75) Inventor: Naoki Ichikawa, Gamagori (JP)

(73) Assignee: Nidek Co., Ltd, Gamagori (JP)

( * ) Notice: Subject to any disclaimer, the term of this patent is extended or adjusted under 35 U.S.C. 154(b) by 433 days.

(21) Appl. No.: 10/996,473

(22) Filed: Nov. 26, 2004

(65) Prior Publication Data

US 2005/0117115 A1 Jun. 2, 2005

(30) Foreign Application Priority Data

Nov. 28, 2003 (JP) ............... 2003-400196

(51) Int. Cl.
*A61B 3/14* (2006.01)
(52) U.S. Cl. .............. 351/206; 351/208; 351/211
(58) Field of Classification Search ........... 351/206, 351/221
See application file for complete search history.

(56) References Cited

U.S. PATENT DOCUMENTS

| 6,022,108 | A | 2/2000 | Yoshida et al. | |
|---|---|---|---|---|
| 6,669,339 | B2 | 12/2003 | Nanjyo | |
| 2001/0028440 | A1 | 10/2001 | Iwanaga | |
| 2004/0169818 | A1* | 9/2004 | Hoshino | 351/205 |
| 2006/0082728 | A1* | 4/2006 | Kushida | 351/211 |
| 2007/0013867 | A1* | 1/2007 | Ichikawa | 351/208 |

FOREIGN PATENT DOCUMENTS

| EP | 1 138 256 A2 | 10/2001 |
|---|---|---|
| EP | 1 452 128 A1 | 9/2004 |
| JP | 08-275921 A | 10/1996 |
| JP | A 2000-5131 | 1/2000 |
| JP | 2000-287936 A | 10/2000 |
| JP | 2001-346764 A | 12/2001 |
| JP | 2003-088503 A | 3/2003 |
| JP | 2003-245253 A | 9/2003 |
| WO | WO 03/049607 A1 | 6/2003 |

* cited by examiner

*Primary Examiner*—Jordan M. Schwartz
(74) *Attorney, Agent, or Firm*—Oliff & Berridge, PLC (57) ABSTRACT

A fundus camera that performs alignment easily and efficiently, and photographing a fundus favorably. A fundus camera has a photographing part in which a fundus photographing optical system is arranged, a fundus observation optical system having a first image-pickup element which picks up an image of the fundus, an anterior-segment observation optical system having a second image-pickup element which picks up an image of an anterior-segment of the eye, a display unit capable of displaying the image of the fundus picked up by the first image-pickup element and the image of the anterior-segment picked up by the second image-pickup element, and a control part which obtains information on alignment of the photographing part with the eye and decides which of the image of the fundus and the image of the anterior-segment is to be displayed on the display unit.

7 Claims, 8 Drawing Sheets

FUNDUS CAMERA

BACKGROUND OF THE INVENTION

1. Field of the Invention

The present invention relates to a fundus camera for photographing a fundus of an eye of an examinee.

2. Description of Related Art

Conventionally, there is known a fundus camera where rough alignment of a photographing part with an eye of the examinee is firstly performed while an image of an anterior-segment of the eye displayed on a monitor is observed, and then fine alignment with a fundus portion to be photographed is performed while an image of a fundus of the eye displayed on the monitor through display switching is observed.

Further, there is known a fundus camera which projects target light for working distance detection onto a cornea of an eye of an examinee, and fine alignment is performed while a corneal reflex of the target light (a working dot) is observed along with an image of a fundus of the eye.

However, rich experience is required to make proper display switching between the image of the anterior-segment and the image of the fundus for alignment, and an inexperienced person takes time and trouble to photograph the fundus favorably. For example, during the alignment while the image of the fundus is observed, if the eye of the examinee greatly moves, the image of the anterior-segment must be displayed again to perform the alignment while the image of the anterior-segment is observed. The same problem arises in the case of the alignment while the working dot is observed.

SUMMARY OF THE INVENTION

An object of the invention is to overcome the problems described above and to provide a fundus camera capable of performing alignment easily and efficiently, and photographing a fundus favorably.

To achieve the objects and in accordance with the purpose of the present invention, a fundus camera has a photographing part in which a fundus photographing optical system is arranged, a fundus observation optical system having a first image-pickup element which picks up an image of the fundus, an anterior-segment observation optical system having a second image-pickup element which picks up an image of an anterior-segment of the eye, a display unit capable of displaying the image of the fundus picked up by the first image-pickup element and the image of the anterior-segment picked up by the second image-pickup element, and a control part which obtains information on alignment of the photographing part with the eye and decides which of the image of the fundus and the image of the anterior-segment is to be displayed on the display unit.

In another aspect of the present invention, a fundus camera has a photographing part in which a fundus photographing optical system is arranged, a moving unit which moves the photographing part, a fundus observation optical system having a first image-pickup element which picks up an image of the fundus, an anterior-segment observation optical system having a second image-pickup element which picks up an image of an anterior-segment of the eye, a display unit capable of displaying the image of the fundus picked up by the first image-pickup element and the image of the anterior-segment picked up by the second image-pickup element, and a control part which obtains information on alignment of the photographing part with the eye, controls the moving unit based on the obtained alignment information so that an alignment state of the photographing part with the eye satisfies a first reference condition, and when the alignment state satisfies the first reference condition, controls the display unit to make display switching from the image of the anterior-segment to the image of the fundus.

Additional objects and advantages of the invention are set forth in the description which follows, are obvious from the description, or may be learned by practicing the invention. The objects and advantages of the invention may be realized and attained by the fundus camera in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
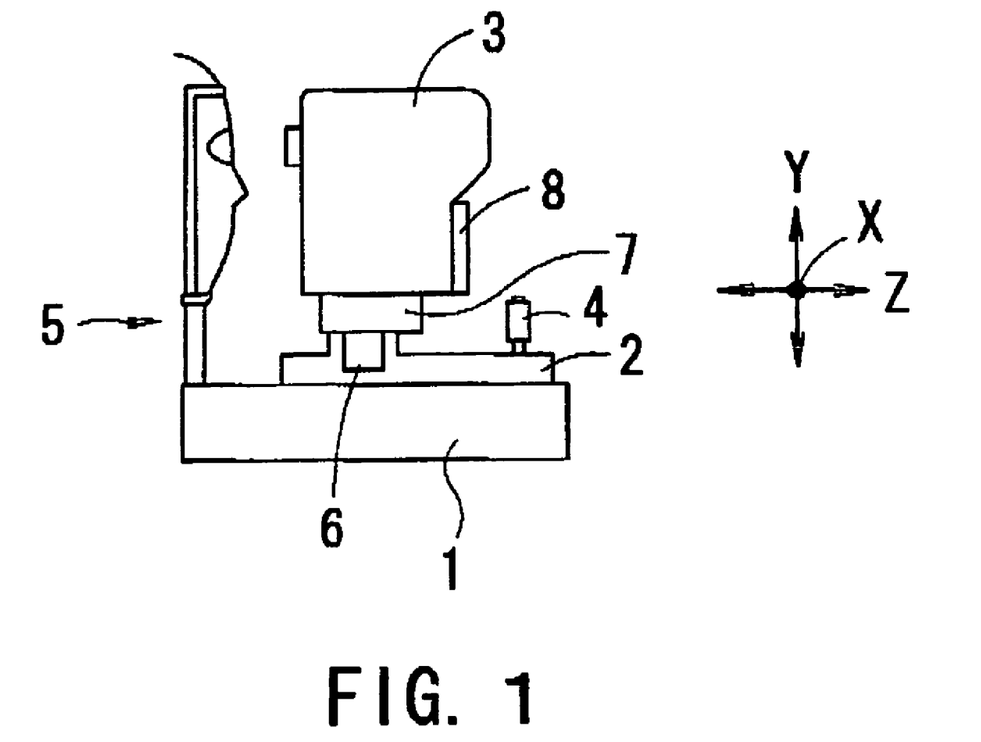
FIG. 1 is a view showing a schematic configuration of a fundus camera.

A detailed description of one preferred embodiment of a fundus camera embodied by the present invention is provided below with reference to the accompanying drawings. FIG. 1 is a view showing a schematic configuration of a fundus camera of non-mydriasis type consistent with the preferred embodiment of the present invention.

The fundus camera is provided with a base 1, a mobile base 2 movable in a right/left direction (hereinafter referred to as an "X-direction") and a back/forth direction (hereinafter referred to as a "Z-direction") with reference to the base 1 through tilting operation of a joystick 4, a photographing part 3 movable in the right/left direction, an up/down direction (hereinafter referred to as a "Y-direction"), and the back/forth direction with reference to the mobile base 2 under control of a control part 81 described later, and a face support part 5 fixedly arranged on the base 1 for supporting a face (a head) of an examinee. A Z table movable in the Z-direction is arranged on a Y table, an X table movable in the X-direction is arranged on the Z table, and the photographing part 3 is arranged on the X table. The X- and Z-moving unit 7 moves the X and Z tables by their respective moving mechanisms consisting of a motor and the like to move the photographing part 3 in the X- and Z-directions. A Y-moving unit 6 moves the y table by its moving mechanism consisting of a motor and the like to move the photographing part 3 in the Y-direction. Besides, for this kind of three-dimensional moving mechanism, a known mechanism may be employed. Further, the photographing part 3 is moved in the Y-direction also by actuating the Y-moving unit 6 through rotational operation of the joystick 4. A monitor 8 for displaying an observation image and a photographed image is provided on an examiner's side of the photographing part 3.

Figure 2:
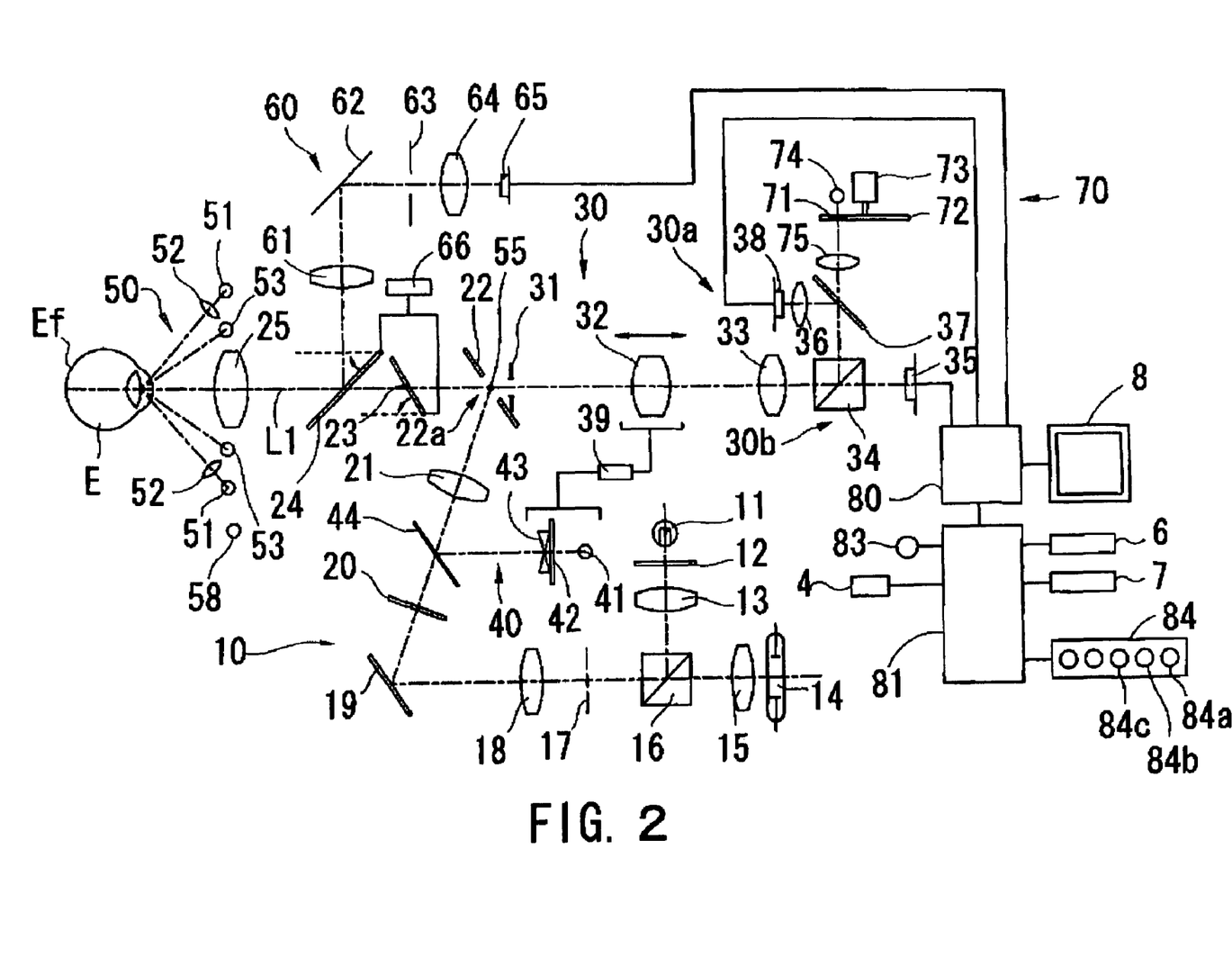
FIG. 2 is a view showing a schematic configuration of an optical system and a control system of the fundus camera.

FIG. 2 is a view showing a schematic configuration of an optical system and a control system housed in the photographing part 3. The optical system generally consists of an illumination optical system 10, a fundus observation/photographing optical system 30, a focus target projection optical system 40, an alignment target projection optical system 50, an anterior-segment observation optical system 60 and a fixation target presenting optical system 70.

<Illumination Optical System 10>

The illumination optical system 10 includes an illumination optical system for fundus observation and an illumination optical system for photographing. Illumination light emitted from an illumination light source 11 for fundus observation such as a halogen light is made into infrared illumination light by an infrared transmission filter 12 which transmits light within an infrared wavelength range of approximately 750 nm to approximately 880 nm, and reflected by a dichroic mirror 16 via a condenser lens 13. The dichroic mirror 16 has a wavelength-selecting property of reflecting approximately all light within an infrared wavelength range and transmitting approximately all light within a visible wavelength range. The infrared illumination light reflected by the dichroic mirror 16 passes through a slit plate 17, a relay lens 18, a reflection mirror 19, a black dot plate 20 having a black dot at its center, a half mirror 44 and a relay lens 21, and is reflected by an apertured mirror 22 to be projected onto a fundus Ef of an eye E of the examinee via an objective lens 25. The slit plate 17 has a pinhole aperture at its center part (i.e., on an optical axis) with a ring-slit aperture therearound. Besides, an infrared light source such as an infrared light-emitting diode may be used instead of the light source 11 such as a halogen light and the infrared transmission filter 12.

Visible illumination light emitted from a visible illumination light source 14 for photographing such as a flash light passes through a condenser lens 15 and is transmitted through the dichroic mirror 16 to be projected onto the fundus Ef via the slit plate 17 to the objective lens 25.

<Fundus Observation/Photographing Optical System 30>

The fundus observation/photographing optical system 30 includes a fundus observation optical system 30a and a photographing optical system 30b. The infrared light and the visible light reflected from the fundus Ef pass through the objective lens 25, an aperture 22a in the apertured mirror 22, a photographing diaphragm 31 arranged in the vicinity of the aperture 22a, a focusing lens 32 and an image forming lens 33 to enter a dichroic mirror 34. The photographing diaphragm 31 is arranged in a position approximately conjugate with a pupil of the eye E with reference to the objective lens 25. The focusing lens 32 is arranged movably by a moving mechanism 39 consisting of a motor and the like, in a direction of an optical axis L1 of the fundus observation/photographing optical system 30 (i.e., an optical axis of the objective lens 25). The dichroic mirror 34 has a wavelength-selecting property of reflecting approximately all light within the infrared wavelength range, and reflecting a part (a small proportion) of light within the visible wavelength range and transmits the other part (a large proportion). The visible reflection light transmitted through the dichroic mirror 34 is photo-received on a CCD camera 35 for photographing having sensitivity to the visible wavelength range to form an image of the fundus Ef. Also, the infrared reflection light reflected by the dichroic mirror 34 is reflected by a dichroic mirror 37, and photo-received on a CCD camera 38 for fundus observation having sensitivity to the infrared wavelength range via a relay lens 36 to form an image of the fundus Ef. The dichroic mirror 37 has a wavelength-selecting property of reflecting approximately all light within the infrared wavelength range, and reflecting a part (a small proportion) of light within the visible wavelength range and transmits the other part (a large proportion). Besides, the CCD camera 38 doubles as image-pickup means for focus target detection to be described later (i.e., the fundus observation optical system doubles as a focus target detection optical system), and picks up the image of the fundus Ef formed by the light source 11 and an image of the focus target formed by the focus target projection optical system 40 to be described later. Incidentally, while it is advantageous to use focus target detection means doubling as fundus image pick-up means as the present embodiment, a dedicated one may be arranged.

Figure 4:
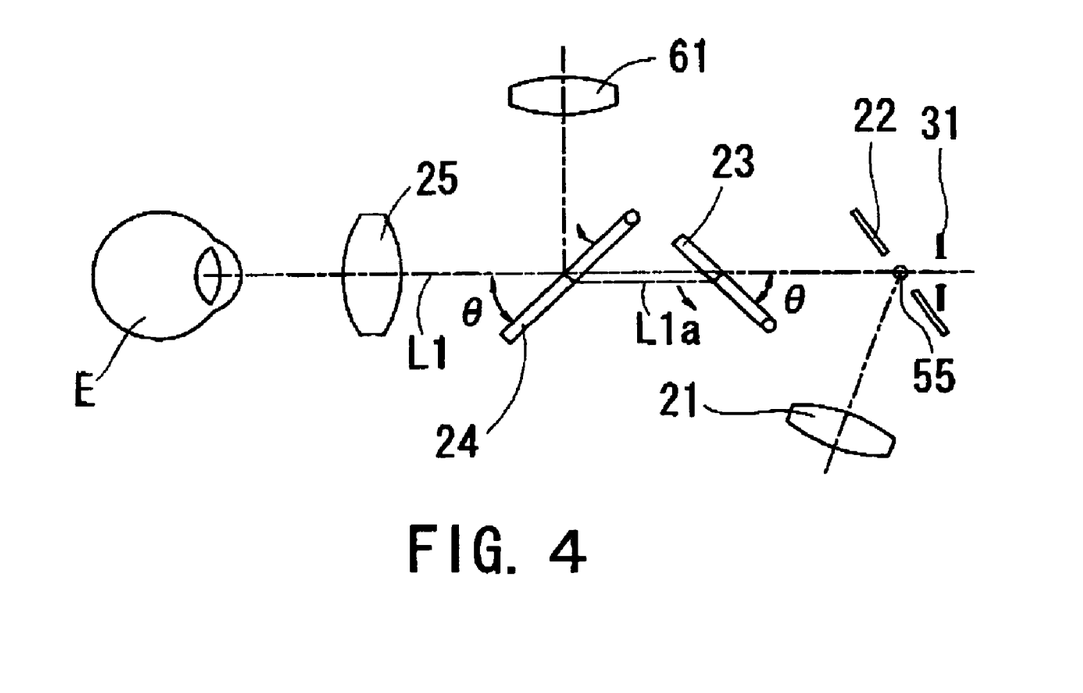
FIG. 4 is a view showing an occurrence of a deviation of an optical axis by insertion of an optical path dividing member, and correction thereof by insertion of a glass plate.

On an optical path between the objective lens 25 and the apertured mirror 22 (the diaphragm 31), a movable dichroic mirror 24 is arranged as an optical path dividing member. Further, on an optical path between the dichroic mirror 24 and the apertured mirror 22 (the diaphragm 31), a movable parallel glass plate 23 is arranged as a member for correcting a deviation of an optical axis caused by the dichroic mirror 24. The dichroic mirror 24 has a wavelength-selecting property of reflecting light within an infrared wavelength range of approximately 900 nm or more including light from an infrared illumination light source 58 for anterior-segment observation and that from the alignment target projection optical system 50 to be described later, and transmitting light within an infrared wavelength range of approximately 900 nm or less including light from the illumination optical system for fundus observation and that from the focus target projection optical system 40 to be described later. The, glass plate 23 has approximately the same thickness and refractive index as the dichroic mirror 24. Further, as shown in FIG. 4, the dichroic mirror 24 is arranged to have an angle of inclination of θ with respect to the optical axis L1, and the glass plate 23 is arranged to have an angle of inclination of 180° minus θ with respect to the optical axis L1. At the time of photographing, the dichroic mirror 24 and the glass plate 23 are flipped up synchronously by an inserting/removing mechanism 66 to be removed from the optical path. Besides, a known mechanism such as a solenoid and cam (or motor and the like) may be used for the inserting/removing mechanism 66.

<Focus Target Projection Optical System 40>

Infrared target light emitted from an infrared light source 41 for focus target projection such as an infrared light-emitting diode passes through a slit target plate 42 and two deflection-angle prisms 43 attached to the target plate 42, is reflected by the half mirror 44, and further passes through the relay lens 21 to the objective lens 25 to be projected onto the fundus Ef (i.e., a focus target is projected thereon). The light source 41 and the target plate 42 are moved in synchronization with the focusing lens 32 in the optical axis direction by the moving mechanism 39. Incidentally, the light source 41 emits infrared light having a center wavelength of approximately 880 nm.

<Alignment Target Projection Optical System 50>

The alignment target projection optical system 50 includes a pair of first projection optical systems having optical axes arranged laterally symmetrical with respect to the optical axis L1, and a pair of second projection optical systems having optical axes arranged laterally symmetrical with respect to the optical axis L1 forming an angle smaller than the optical axes of the first projection optical systems. A pair of the first projection optical systems include infrared light sources 51 such as infrared light-emitting diodes which emit infrared light having a center wavelength of approximately 940 nm and collimating lenses 52, respectively, and project infrared target light at an infinite distance onto the eye E with approximately parallel light (i.e., alignment targets are projected thereon). On the other hand, a pair of the second projection optical systems include infrared light sources 53 such as infrared light-emitting diodes which emit infrared light having a center wavelength of approximately 940 nm, and projects infrared target light at a finite distance onto the eye E with divergent light (i.e., alignment targets are projected thereon). Besides, the optical systems in FIG. 2 are viewed from the side. The alignment target projection optical system 50 is presented as if it is arranged vertically; however, it is actually arranged laterally.

Figure 3:
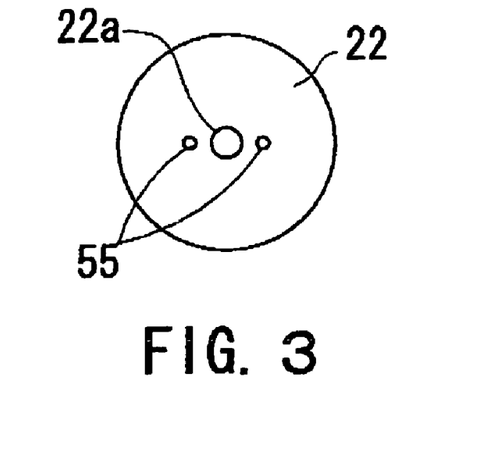
FIG. 3 is a view showing an arrangement of light sources for forming working dots.

Further, as shown in FIG. 3, around the aperture 22a in the apertured mirror 22, two infrared light sources 55 which project infrared target light having a center wavelength of approximately 880 nm for forming working dots are arranged laterally symmetrical with respect to the optical axis L1. Incidentally, the light sources 55 may also be configured by arranging an end face of an optical fiber in the vicinity of the apertured mirror 22 and directing infrared light to the optical fiber. In addition, the light sources 55 are arranged so that, when a working distance between the eye E and the objective lens 25 becomes appropriate, a conjugate position is at a distance equivalent to a half of a corneal radius of curvature of the eye E.

<Anterior-Segment Observation Optical System 60>

Infrared illumination light emitted from the infrared illumination light source 58 for anterior-segment observation such as an infrared light-emitting diode is reflected by an anterior-segment of the eye E and the dichroic mirror 24, passes through a field lens 61, a reflection mirror 62, a diaphragm 63 and a relay lens 64, and is photo-received on a CCD camera 65 for anterior-segment observation having sensitivity to the infrared wavelength range to form an image of the anterior-segment of the eye E. Besides, the light source 58 emits infrared light having a center wavelength of approximately 940 nm. Further, the CCD camera 65 doubles as image-pickup means for alignment target detection (i.e., the anterior-segment observation optical system 60 doubles as an alignment target detection optical system), and picks up the image of the anterior-segment of the eye E formed by the light source 58 and images of the alignment targets formed by the alignment target projection optical system 50. Incidentally, while it is advantageous to use alignment target detection means doubling as anterior-segment image pick-up means as the present embodiment, a dedicated one may be arranged.

<Fixation Target Presenting Optical System 70>

Red fixation target light emitted from a fixation target light source (a fixation lamp) 74 such as a red light-emitting diode passes through an aperture in a shielding plate 71 of a rotary disk 72 and a relay lens 75 to be transmitted through the dichroic mirror 37. A part of the red fixation target light transmitted through the dichroic mirror 37 is reflected by the dichroic mirror 34, and passes through the image forming lens 33 to the objective lens 25 to be projected onto the fundus Ef (i.e., a fixation target is projected thereon). The disk 72 is provided with eight shielding plates 71, and the aperture in each shielding plate 71 is either for guiding a visual line so that the vicinity of a posterior pole of the fundus of a right eye comes to a center of photographing, for guiding the visual line so that the vicinity of a posterior pole of the fundus of a left eye comes to the center of photographing, or for guiding the visual line so that a periphery of the fundus is photographed. The disk 72 is rotated by a pulse motor 73, and one of the eight shielding plates 71 is selectively arranged in front of the light source 74. Incidentally, the number of shielding plates 71 is not limited to eight.

Figure 5A:
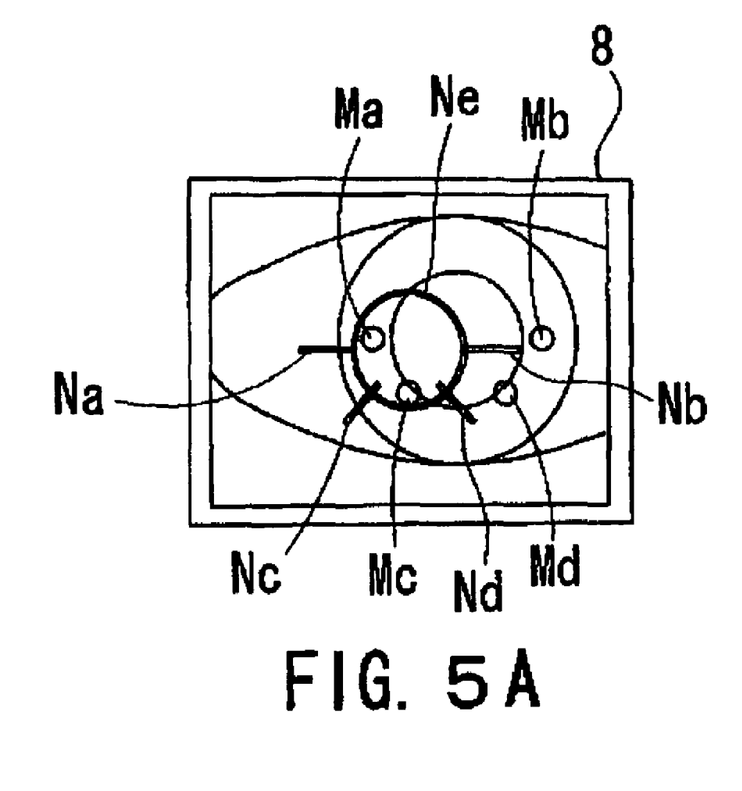
FIGS. 5A and 5B are views showing an example of an observation image of an anterior-segment of an eye.
Figure 5B:
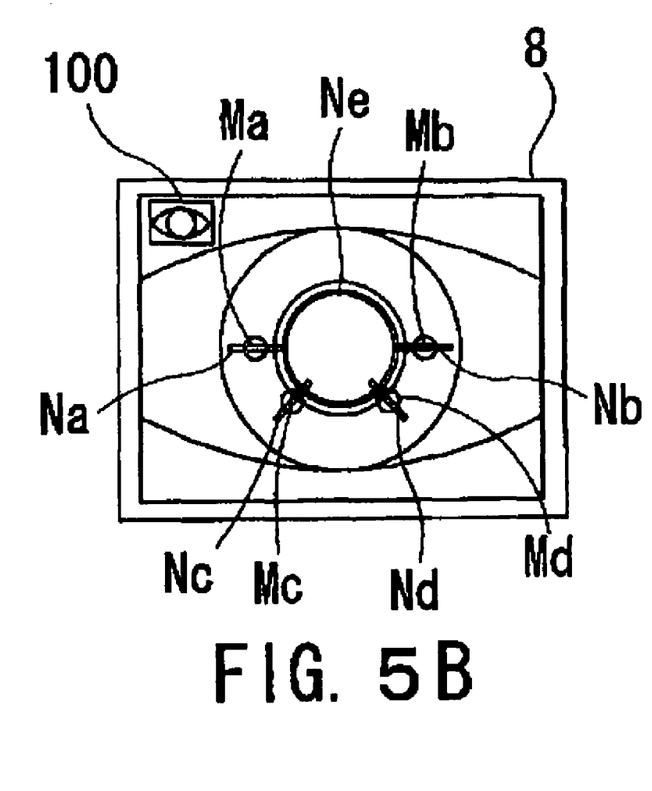

At the time of the anterior-segment observation and the alignment, the dichroic mirror 24 and the glass plate 23 are inserted into the optical path of the fundus observation/photographing optical system 30 (i.e., the optical path between the objective lens 25 and the apertured mirror 22). The image of the anterior-segment formed by the light source 58 and the images of the alignment targets formed by the alignment target projection optical system 50 are reflected by the dichroic mirror 24 and picked up by the CCD camera 65. FIGS. 5A and 5B show the anterior-segment image and the alignment target images picked up by the CCD camera 65 and displayed on the monitor 8. Target images Ma and Mb are the alignment target images at an infinite distance formed by the first projection optical systems, and target images Mc and Md are the alignment target images at a finite distance formed by the second projection optical systems. The second projection optical systems are arranged so that the target images Mc and Md are formed below the target images Ma and Mb.

Also at the time of the fundus observation and the focusing, the dichroic mirror 24 and the glass plate 23 are inserted into the optical path of the fundus observation/photographing optical system 30. The image of the fundus Ef formed by the illumination optical system for fundus observation and the image of the focus target formed by the focus target projection optical system 40 are transmitted through the dichroic mirror 24 and the glass plate 23 to be picked up by the CCD camera 38. At this time, as shown in FIG. 4, the optical axis L1 is deviated (shifted) to be an optical axis L1a by insertion of the dichroic mirror 24, and it is made back to the optical axis L1 by insertion of the glass plate 23. Therefore, the image of the anterior-segment and the image of the fundus Ef are favorably picked up by the CCD camera 65 and the CCD camera 38, respectively, at a time.

If the glass plate 23 is not arranged (not inserted), the deviated optical axis L1a does not pass through a center of the photographing diaphragm 31. In such a case, a center of the infrared illumination light for fundus observation in a ring shape reflected from the anterior-segment deviates from the center of the photographing diaphragm 31, and the infrared light reflected from the anterior-segment comes to enter the CCD camera 38 for fundus observation even in a state where the alignment is completed. As a result, a flare tends to appear in the image of the fundus Ef (observation image). Further, the image of the focus target cannot be accurately detected.

At the time of the photographing, the dichroic mirror 24 and the glass plate 23 are removed from the optical path by the inserting/removing mechanism 66. The image of the fundus Ef is picked up by the CCD camera 35 via the objective lens 25 to the dichroic mirror 34. Besides, such a constitution may be employed that the CCD camera 35 for photographing doubles as the camera for fundus observation.

Respective image signals outputted from the CCD cameras 65, 38 and 35 are inputted to an image processing part 80. The image processing part 80 detects the images of the alignment targets based on the image signal from the CCD camera 65 and the image of the focus target based on the image signal from the CCD camera 38. Further, the image processing part 80 is connected to the monitor 8 to control images displayed thereon. The control part 81 is connected with the image processing part 80, the Y-moving part 6, the X- and Z-moving part 7, the joystick 4, the moving mechanism 39, the inserting/removing mechanism 66, the pulse motor 73, a photographing switch 83, a switch part 84 having various switches, the respective light sources, and the like. (In FIG. 2, a part of connection lines are not illustrated.)

Figure 9:
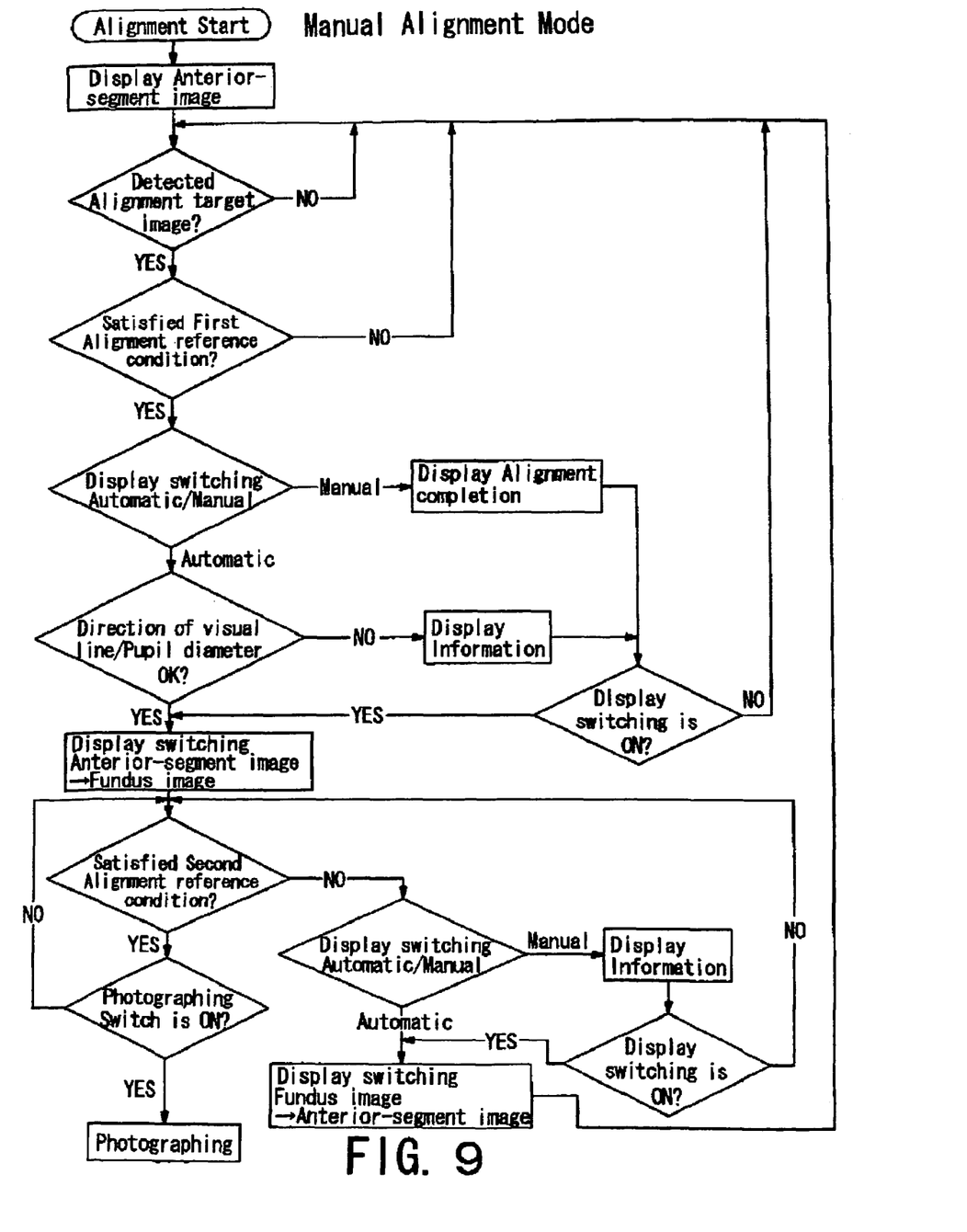
FIG. 9 is a flowchart showing operation in a manual alignment mode.

In the apparatus having a constitution as above, operation thereof will be described hereinafter. Firstly, operation in a manual alignment mode will be described referring to a flowchart shown in FIG. 9, where the examiner operates the joystick 4 to align the photographing part 3 with the eye E. In this case, the manual alignment mode is previously selected by a switch 84a in the switch part 84.

First, the face of the examinee is supported by the face support part 5. In the initial stage, the dichroic mirror 24 and the glass plate 23 are inserted into the optical path of the fundus observation/photographing optical system 30, and the image of the anterior-segment picked up by the CCD camera 65 is displayed on the monitor 8. While observing the image of the anterior-segment displayed on the monitor 8, the examiner moves the photographing part 3 in the X- and Y-directions so that the image of the anterior-segment is placed in the center of a screen on the monitor 8. In addition, the examiner moves the photographing part 3 in the Z-direction to bring the image of the anterior-segment into focus. When the image of the anterior-segment comes to place in the center of the screen on the monitor 8, as shown in FIG. 5A, the four target images Ma, Mb, Mc and Md come to be displayed (reflected). In FIG. 5A, reference letters Na, Nb, Nc and Nd indicate reticle marks respectively in a line shape, and a reference letter Ne indicates a ring mark for indicating a pupil diameter necessary for the photographing, all of which are electrically formed by the image processing part 80. As shown in FIG. 5B, the alignment is made by moving the photographing part 3 in the X- and Y-directions so that the target images Ha, Mb, Mc and Md are respectively placed on the reticle marks 1a, Nb, Nc and Nd. Further, the photographing part 3 is moved in the Z-direction to bring the target images Ma to Md into focus.

Figure 6:
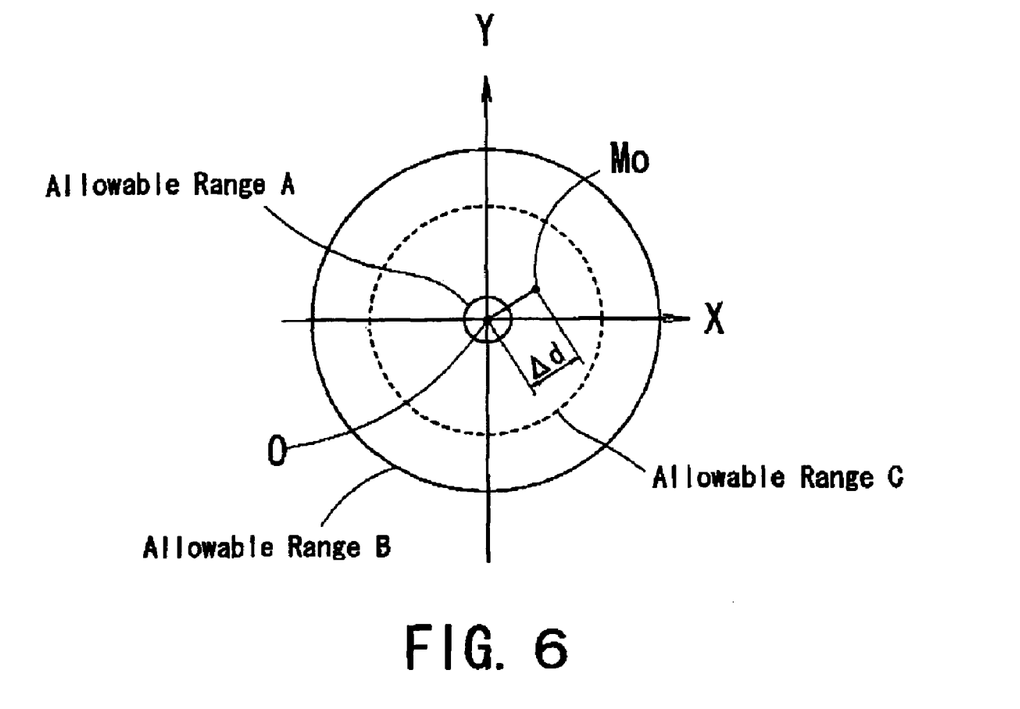
FIG. 6 is a view showing an example of a reference condition for alignment.

When the target images Ma to Md picked up by the CCD camera 65 are detected by the image processing part 80, the control part 81 obtains information on an alignment state in the X-, Y- and Z-directions based on the target images Ma to Md. That is to say, the control part 81 obtains, as shown in FIG. 6, a deviation (shift) amount Δd with reference to an alignment reference position O in the X- and Y-directions while defining the midpoint between the target images Ma and Mb as a corneal vertex position Mo. Then, the control part 81 judges appropriateness of the alignment state in the X- and Y-directions (i.e., alignment completion) based on whether the deviation amount Δd stably falls within a predetermined first allowable range A of alignment completion for a predetermined time (for example, 10 frames of image processing, 0.3 second, or the like) (i.e., a first reference condition for alignment is satisfied) Further, the alignment state in the Z-direction is target images Ma and Mb to a distance between the target images Mc and Md. It utilizes a characteristic that in the case of forming corneal reflexes using light sources at an infinite distance and light sources at a finite distance, respectively, a height of corneal reflexes formed by the light sources at a finite distance is changed as a working distance is changed, while a height of corneal reflexes formed by the light sources at an infinite distance is not changed even when the working distance is changed. (For the details, see U.S. Pat. No. 5,463,430 corresponding to Japanese Patent Application Unexamined Publication No. Hei6-46999.) The control part 81 obtains a deviation (shift) amount with respect to an alignment reference position in the Z-direction, and judges appropriateness of the alignment state in the Z-direction (i.e., alignment completion) based on whether the deviation amount stably falls within a predetermined first allowable range of alignment completion for a predetermined time (i.e., a first reference condition for alignment is satisfied).

If the alignment state in the X-, Y-, and Z-directions satisfies the first reference condition, the display switching is made from the image of the anterior-segment to the image of the fundus Ef. Here, if the display switching is set in a manual switching mode by a switch 84b in the switch part 84, a mark 100 for informing the alignment completion blinks on the monitor 8. Through display of the mark 100, the examiner may be informed that the alignment is proper. Then, the examiner presses a switch 84c in the switch part 84 to make the display switching from the image of the anterior-segment to the image of the fundus Ef. When the switch 84c is pressed, the image of the fundus Ef picked up by the CCD camera 38 is displayed on the monitor 8.

On the other hand, if the display switching is set in an automatic switching mode by the switch 84b, the control part 81 controls to make the display switching from the image of the anterior-segment to the image of the fundus Ef in accordance with the judgment of the alignment completion in the X-, Y-, and Z-directions.

Besides, for making the display switching from the image of the anterior-segment to the image of the fundus Ef upon completion of the alignment, it is preferable that appropriateness of at lease one of a direction of the visual line and the pupil diameter are confirmed.

Figure 7:
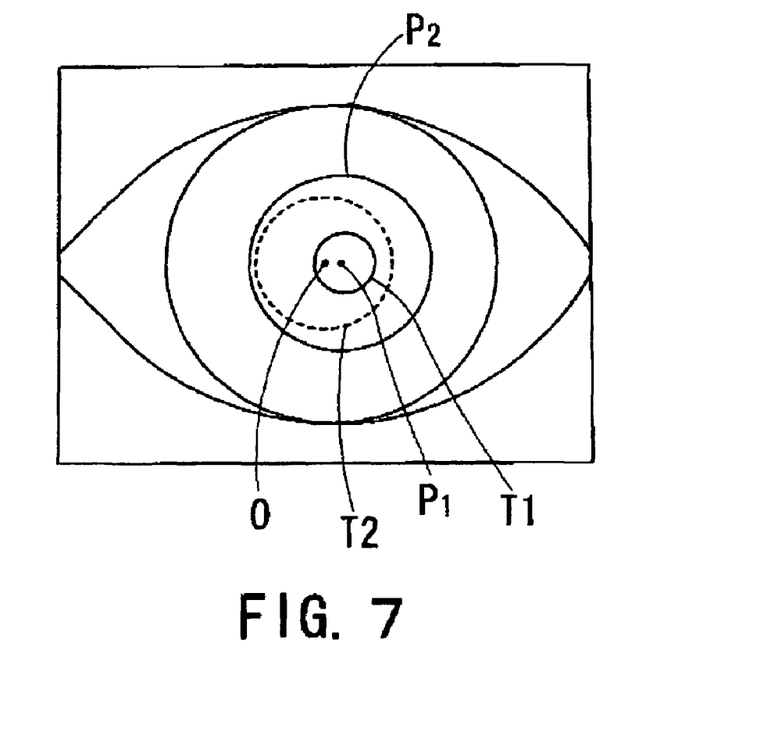
FIG. 7 is a view showing an example of a reference condition for judging appropriateness of a direction of a visual line and a pupil diameter.

An example of judging the appropriateness of the direction of the visual line and the pupil diameter will be described hereinafter. FIG. 7 is an example of the screen showing the image of the anterior-segment when the alignment with the right eye is completed. First, the appropriateness of the direction of the visual line is judged based on whether a pupil center P1 detected from the image of the anterior-segment is stably positioned within an area T1 for judgment of the direction of the visual line for a predetermined time. At the time of the alignment with the right eye, the fixation target which guides the vicinity of the posterior pole of the fundus of the right eye to the center of photographing is previously presented. In a case where the right eye fixates on the presented fixation target, if the pupil center P1 is positioned within the area T1 having its center on a slightly right side of the alignment reference position O, the direction of the visual line is judged to be proper. In a case where the right eye does not fixate on the presented fixation target, the visual line does not settle and goes out of the area T1.

The appropriateness of the pupil diameter is judged based on whether a pupil edge P2 detected from the image of the anterior-segment is larger than an area T2 for judgment of the pupil diameter or not. Size of the area T2 is set with reference to the center of the display on the monitor 8 (an image-pickup optical axis) in such a diameter as to allow the passage of the infrared illumination light for fundus observation and the visible illumination light for photographing (e.g., 4 mm in diameter). If the pupil edge P2 is larger than the area T2, illumination light intensity at the time of photographing is adequately secured, and also the focus target is projected onto the fundus Ef.

In the automatic switching mode, when both the direction of the visual line and the pupil diameter are judged to be proper, the display switching is automatically made from the image of the anterior-segment to the image of the fundus Ef. In the manual switching mode, the mark 100 blinks. Besides, if at least one of the direction of the visual line and the pupil diameter is judged not to be proper, information as such is displayed on the monitor 8 to inform the examiner thereof. With reference to the displayed information, the examiner may previously take necessary measures before the photographing, such as giving notice to the examinee to fixate on the fixation target, having a break so that the pupil diameter becomes larger, or the like.

Figure 8:
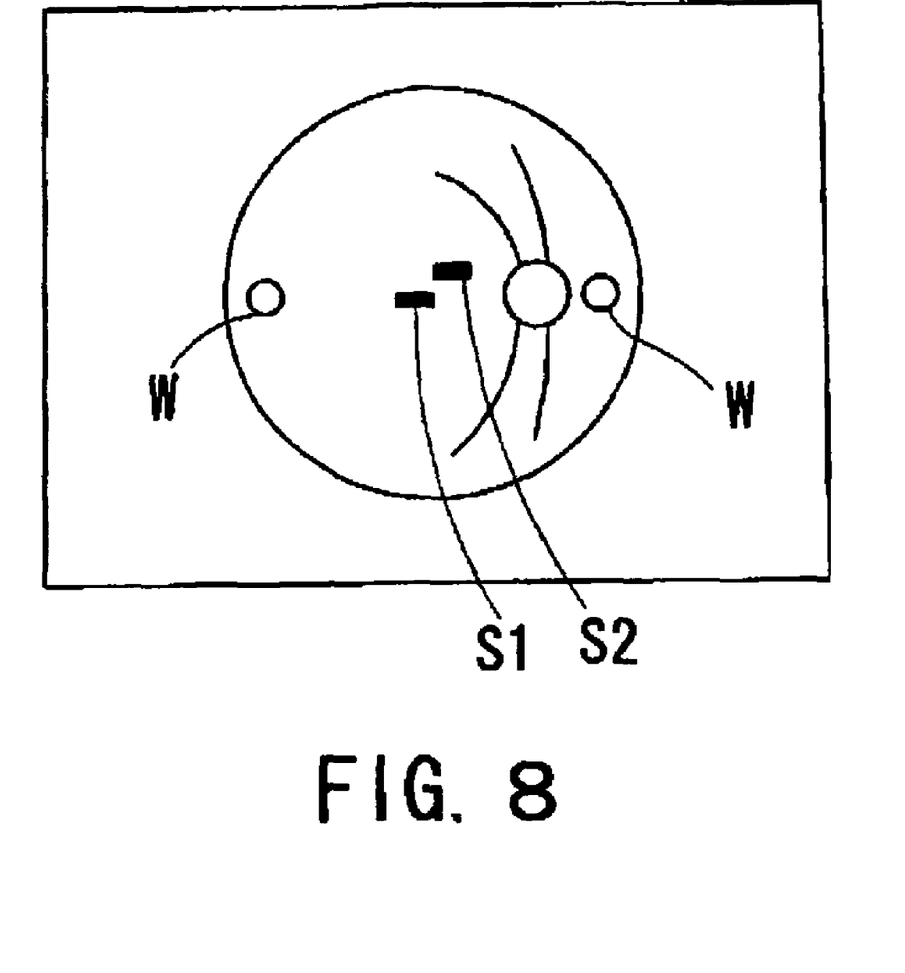
FIG. 8 is a view showing an example of an observation image of a fundus.

FIG. 8 is an example of the screen when the display switching to the image of the fundus Ef is made. When the alignment state is made proper to some extent, two working dots W formed by the light sources 55 come to be displayed. The examiner confirms the focus of the working dots W, a flare in the image of the fundus Ef, and the like while observing the image of the fundus Ef, and further performs alignment through operation of the joystick 4 so that the photographing may be performed in a desired state.

When the eye E greatly moves, the working dots W displayed along with the image of the fundus Ef come not to be displayed. Once the working dots W come not to be displayed, the alignment while observing the image of the fundus Ef becomes difficult to perform.

Therefore, in the present fundus camera, even when the image of the fundus Ef is displayed on the monitor 8, the control part 81 obtains information on the alignment state in the X-, Y-, and Z-directions based on the image signal from the CCD camera 65 for the anterior-segment observation. Once the alignment is completed and the display switching is made from the image of the anterior-segment to the image of the fundus Ef, observation is made to know whether or not the deviation amount Δd in the X- and Y-directions falls within a predetermined second allowable range B of alignment which is set greater than the first allowable range A (i.e., whether or not a second reference condition for alignment is satisfied). The second allowable range B is, for example, a range of ±3-4 mm with respect to the alignment reference position O. If the deviation amount Δd exceeds the second allowable range B, the infrared illumination light becomes difficult to reach the fundus Ef, so that the image of the fundus Ef tends to be unobservable. Similarly, for the Z-direction, observation is made to know whether or not the deviation amount falls within a predetermined second allowable range of alignment which is set greater than the first allowable range for alignment completion (i.e., whether or not a second reference condition for alignment is satisfied). The second allowable range in the Z-direction is set, for example, as a distance out of which the working dots W become unobservable. Further, when the alignment state (deviation amount) in either of the x-, Y-, and Z-directions comes not to satisfy the second reference condition (second allowable range), in the automatic switching mode, the display switching is automatically made from the image of the fundus Ef to the image of the anterior-segment. In the manual switching mode, a mark (unillustrated) informing the switching to the image of the anterior-segment is displayed on the monitor 8 so that the examiner may press the switch 84c to switch from the image of the fundus Ef to the image of the anterior-segment.

After the alignment while the image of the fundus Ef is observed, as shown in FIG. 8, the focus target images S1 and S2 formed by the focus target projection optical system 40 are displayed in the center. Therefore, the light source 41, the target plate 42 and the focusing lens 32 are moved in the optical axis direction based on the target images S1 and S2 for focusing on the fundus Ef. If the fundus Ef is not brought into focus, the target images S1 and S2 are displayed separately, and if the fundus Ef is brought into focus, they are displayed in coincident with each other. While the focusing can be performed manually, the present apparatus is provided with an automatic focusing mechanism. The target images S1 and S2 are detected and processed by the image processing part 80, and their separation information is transferred to the control part 81. Based on the separation information on the target images S1 and S2, the control part 81 drives and controls the movement mechanism 39 so that both the images coincide with each other to perform focusing on the fundus Ef. Upon completion of the focusing, the examiner presses the photographing switch 83 to perform photographing.

When a trigger signal from the switch 83 is inputted, the control part 81 drives and controls the inserting/removing mechanism 66 to remove the dichroic mirror 24 and the glass plate 23 from the optical path, and have the light source 14 emit light. Through the emission from the light source 14, the fundus Ef is illuminated with the visible light, and the light reflected from the fundus Ef is photo-received on the CCD camera 35 to form the image of the fundus Ef. Further, on the monitor 8, the image of the fundus Ef picked up by the CCD camera 35 is displayed in colors. In addition, the image of the fundus Ef (a photographed image) is stored in an image memory included in the image processing part 80.

Figure 10:
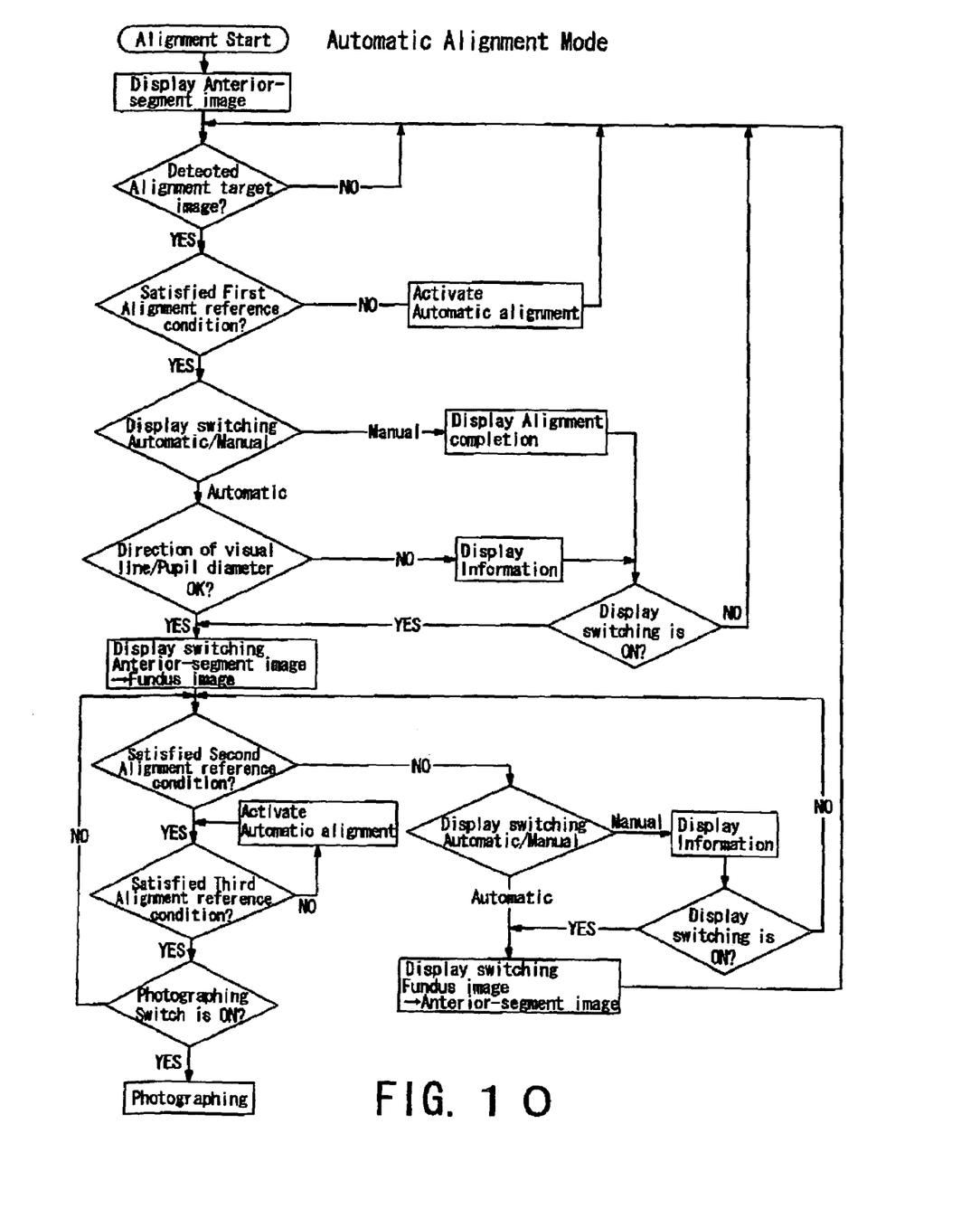
FIG. 10 is a flowchart showing operation in an automatic alignment mode.

Next, operation in a case where an automatic alignment mode is set by the switch 84a will be described referring to a flowchart in FIG. 10.

The examiner performs rough alignment of the photographing part 3 with the eye E through operation of the joystick 4 while observing the image of the anterior-segment displayed on the monitor 8. When the target images Ma to Md picked up by the CCD camera 65 are detected by the image processing part 80, the control part 81 controls to obtain the information on the alignment state in the X-, Y-, and Z-directions based on the target images Ma to Md, and drives and controls the X- and Z-moving part 7 and the Y-moving part 6 to perform automatic alignment so as to satisfy the first reference condition. Then, when the alignment is completed, the control part 81 stops the automatic alignment. Thereafter, as in the case of the manual alignment mode, the control part 81 controls to make the display switching from the image of the anterior-segment to the image of the fundus Ef, based on the setting of whether the display switching is made automatically or manually, and based on the judgment of the appropriateness of the direction of the visual line and the pupil diameter.

Further, after the display switching from the image of the anterior-segment to the image of the fundus Ef, when the alignment state in either of the X-, Y-, and z-directions comes not to satisfy the second reference condition, as in the case of the manual alignment mode, the display switching is made from the image of the fundus Ef to the image of the anterior-segment based on the setting of the display switching.

Here, in the automatic alignment mode, another judgment condition for starting re-implementation of automatic alignment is included, in contrast to the manual alignment mode. The control part 81 makes judgment based on whether or not the deviation amount Δd in the X- and Y-directions falls within a predetermined third allowable range C of alignment which is set greater than the first allowable range A (the third allowable range C is preferably smaller than the second allowable range B) (i.e., whether or not a third reference condition for alignment is satisfied). Same shall apply to the deviation amount Δd in the Z-direction. That is to say, the control part 81 stops the automatic alignment until the deviation amount Δd exceeds the third allowable range, and re-implements the automatic alignment when the deviation amount Δd exceeds the third allowable range. The third allowable range C in the X- and Y-directions is, for example, a range of ±1.5 mm with respect to the alignment reference position O.

As mentioned above, by stopping the automatic alignment after the completion of the alignment, the examiner may perform fine adjustment of the photographing position through operation of the joystick 4 while observing the image of the fundus Ef displayed on the monitor 8. When the display switching is made from the image of the anterior-segment to the image of the fundus Ef, as shown in FIG. 8, the two working dots W formed by the light sources 55 are displayed. The examiner confirms the focus of the working dots W, the flare on the image of the fundus Ef and the like and further performs alignment through operation of the joystick 4 while observing the image of the fundus Ef so that the photographing may be performed in a desired state. In the automatic alignment utilizing the image of the anterior-segment, there is a case where a flare slightly appears on the image of the fundus Ef due to individuality in a cornea and a crystalline lens; however, as the manual alignment may be performed in order to avoid the flare, unfavorable photographing may be prevented. Further, when the alignment state comes not to satisfy the third reference condition, the automatic alignment is performed while displaying the image of the fundus Ef (observation image), so that a burden of the manual alignment is reduced and the alignment may be performed easily.

Furthermore, when the alignment is judged as completed, automatic focusing is implemented. Upon completion of the alignment and the focusing, the photographing switch 83 is pressed to implement the photographing.

Incidentally, as to the display switching between the image of the anterior-segment and the image of the fundus Ef, such a constitution may also be employed that, when switched to a state of anterior-segment observation, the image of the anterior-segment is largely displayed and the image of the fundus is displayed on a small screen synthetically, and when switched to a state of fundus observation, the image of the fundus Ef is largely displayed and the image of the anterior-segment is displayed on the small screen synthetically.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an eye of an examinee, the fundus camera comprising:
   a photographing part in which a fundus photographing optical system is arranged;
   a fundus observation optical system having a first image-pickup element which picks up an image of the fundus;
   an anterior-segment observation optical system having a second image-pickup element which picks up an image of an anterior-segment of the eye;
   a display unit capable of displaying the image of the fundus picked up by the first image-pickup element and the image of the anterior-segment picked up by the second image-pickup element; and
   a control part which obtains information on alignment of the photographing part with the eye and decides which of the image of the fundus and the image of the anterior-segment is to be displayed on the display unit,
   wherein the control part controls the display unit to make display switching from the image of the anterior-segment to the image of the fundus and make display switching from the image of the fundus to the image of the anterior-segment; and
   wherein the control part makes the display switching from the image of the anterior-segment to the image of the fundus when an alignment deviation of the photographing part with the eye falls within a first allowable range, and after the display switching from the image of the anterior-segment to the image of the fundus, makes the display switching from the image of the fundus to the image of the anterior-segment when the alignment deviation of the photographing part with the eye exceeds a second allowable range which is set greater than the first allowable range.

2. The fundus camera according to claim 1, wherein the control part judges completion of the alignment based on the obtained alignment information, determines appropriateness of at least one of a direction of a visual line and a state of a pupil of the eye at the time of the completion of the alignment based on an output from the second image-pickup element, and decides which of the image of the fundus and the image of the anterior-segment is to be displayed on the display unit based on a result of the determination.

3. The fundus camera according to claim 1, wherein the control part obtains the information on alignment of the photographing part with the eye based on an output from the second image-pickup element.

4. The fundus camera according to claim 3, further comprising a target projection optical system for projecting a target for alignment onto the anterior-segment of the eye,
   wherein the second image-pickup element picks up an image of the target formed on the anterior-segment of the eye.

5. A fundus camera for photographing a fundus of an eye of an examinee, the fundus camera comprising:
   a photographing part in which a fundus photographing optical system is arranged;
   a moving unit which moves the photographing part;
   a fundus observation optical system having a first image-pickup element which picks up an image of the fundus;

an anterior-segment observation optical system having a second image-pickup element which picks up an image of an anterior-segment of the eye;

a display unit capable of displaying the image of the fundus picked up by the first image-pickup element and the image of the anterior-segment picked up by the second image-pickup element; and a control part which obtains information on alignment of the photographing part with the eye, controls the moving unit based on the obtained alignment information so that an alignment deviation of the photographing part with the eye falls within a first allowable range, and when the alignment deviation falls within the first allowable range, controls the display unit to make display switching from the image of the anterior-segment to the image of the fundus, wherein, after the display switching from the image of the anterior-segment to the image of the fundus, the control part controls the display unit to make display switching from the image of the fundus to the image of the anterior-segment when the alignment deviation exceeds a second allowable range which is set greater than the first allowable range.

6. The fundus camera according to claim 5, wherein the control part obtains the information on alignment of the photographing part with the eye based on an output from the second image-pickup element.

7. The fundus camera according to claim 6, further comprising a target projection optical system for projecting a target for alignment onto the anterior-segment of the eye, wherein the second image-pickup element picks up an image of the target formed on the anterior-segment of the eye.

* * * * *